United States Patent [19]
Angelo

[11] Patent Number: 5,370,673
[45] Date of Patent: Dec. 6, 1994

[54] COUNTER-BALANCED PIVOTALLY MOUNTED TANNING UNIT

[75] Inventor: Gary P. Angelo, Jonesboro, Ark.
[73] Assignee: Sun Industries, Inc., Jonesboro, Ark.
[21] Appl. No.: 613,111
[22] Filed: Nov. 14, 1990
[51] Int. Cl.⁵ ............................................. A61N 5/06
[52] U.S. Cl. ...................................................... 607/90
[58] Field of Search ............... 128/376, 371, 395, 396; 362/402; 248/597, 162.1, 655; 250/504 R

[56] References Cited

U.S. PATENT DOCUMENTS

| | | | |
|---|---|---|---|
| 4,651,263 | 3/1987 | Hancock | 128/371 |
| 4,660,561 | 4/1987 | Nielsen | 128/396 |
| 4,683,886 | 8/1987 | Kramer et al. | 128/396 |
| 4,918,319 | 4/1990 | Kruithof | 250/504 R |

FOREIGN PATENT DOCUMENTS

| | | | |
|---|---|---|---|
| 3005487 | 8/1981 | Germany | 128/396 |
| 3017355 | 11/1981 | Germany | 128/395 |
| 3037775 | 5/1982 | Germany | 128/396 |
| 3129486 | 2/1983 | Germany | 128/396 |
| 3303794 | 8/1984 | Germany | 128/395 |
| 3443045 | 5/1986 | Germany | 250/504 R |
| 4001666 | 8/1990 | Germany | 128/395 |
| 8503406 | 7/1987 | Netherlands | 128/395 |

Primary Examiner—Mark S. Graham
Attorney, Agent, or Firm—Crutsinger & Booth

[57] ABSTRACT

The present invention provides an apparatus for counter-balancing a tanning unit pivotally mounted to a base and having a radiation energy source for artificially tanning a person. The apparatus comprises a base, a tanning unit pivotally mounted to said base, and a device for variably applying torque to said tanning unit so that, throughout the range of rotational motion of said tanning unit, the instantaneous applied torque produced by said device for applying torque to said tanning unit approximately counter-balances the instantaneous torque produced by gravitational forces acting on said tanning unit. Therefore, said tanning unit may be retained in any instantaneous position between a raised position and a lowered position. Said device for variably applying torque to said tanning unit comprises an urging device connected between said tanning unit and said base which provides a variable force vector having a force magnitude, proportional to the deformation of said urging device.

10 Claims, 5 Drawing Sheets

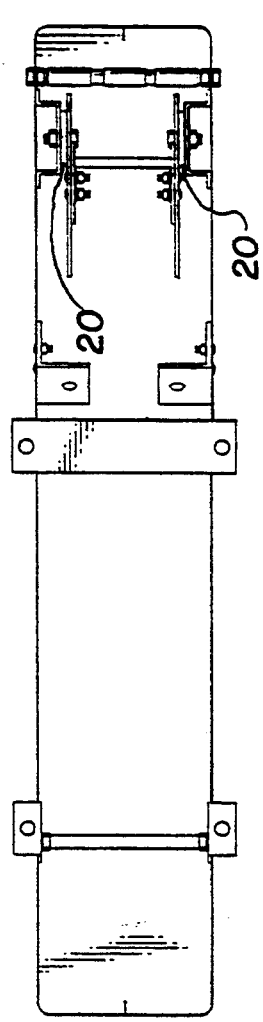
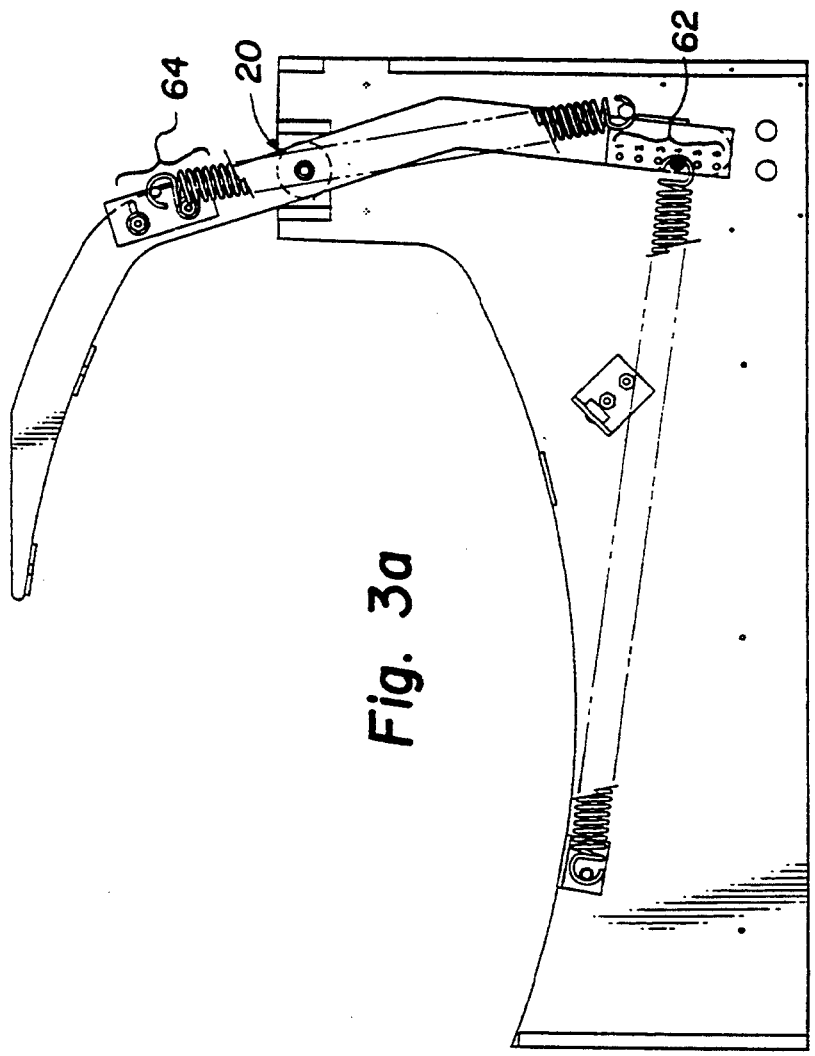
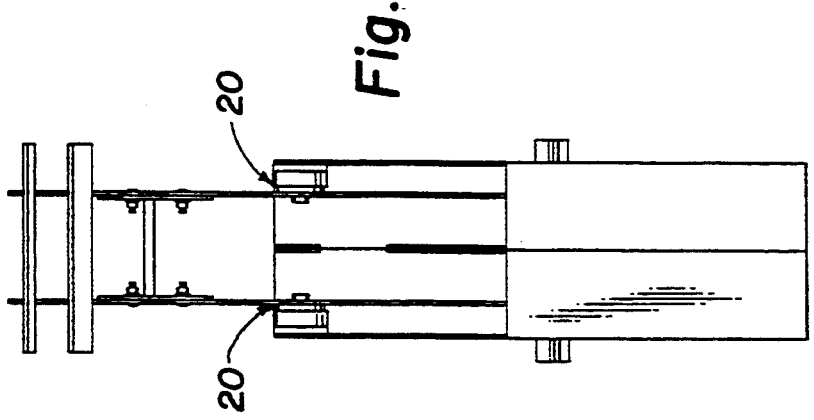
Fig. 3a
Fig. 3b
Fig. 3c

COUNTER-BALANCED PIVOTALLY MOUNTED TANNING UNIT

TECHNICAL FIELD

The present invention provides an apparatus for counter-balancing a tanning unit pivotally mounted to a base and having a radiation energy source for artificially tanning a person.

BACKGROUND OF THE INVENTION

The heavy top tanning unit of a tanning bed is difficult for many people to raise and lower. A simple hinge mechanism on the tanning unit restrains the motion of the tanning unit to rotation about the axis of the hinge. The top tanning unit is to be moved by applying a force to the top tanning unit such that a sufficient torque is produced about the axis of the hinge to over-balance the torque caused by gravitational forces acting on the mass of the tanning unit. A person can direct the force required to raise the tanning unit about the axis of the hinge to maximize the torque. Therefore, a simple hinge mechanism can be an efficient means of lifting or lowering a tanning unit.

When the tanning unit is massive, however, the force required to lift the tanning unit or to gently lower the tanning unit is great. The abstract efficiency of the hinge is little consolation to a person trying to handle a heavy hinged tanning unit.

Furthermore, some people are claustrophobic and do not like to have the tanning unit in the fully lowered position. Therefore, it would be a valuable contribution to the art to provide a tanning unit which can be retained in any instantaneous position between a first lowered position and a second raised position.

Finally, traditional mechanisms for supporting the top unit of a tanning bed are obtrusive and unreliable. Most of the current mechanisms employ gas cylinders which are highly sensitive to the ambient temperature. Therefore, these mechanisms work over a rather narrow temperature range. The tanning unit radiates sufficient heat that the ambient temperature fluctuates significantly. It is extremely irritating to the person using the tanning unit when the tanning unit will not stay in a desired position. These gas cylinders are usually attached toward the front of the tanning unit which interferes with free access to the tanning bed.

SUMMARY OF THE INVENTION

It is an object of the present invention to provide an apparatus for counter-balancing heavy pivotally mounted tanning units for retaining the tanning unit is any instantaneous position between a raised position and a lowered position. The weight of the heavy tanning unit is counter-balanced by at least one, preferably two, means for variably applying torque to said tanning unit. Throughout the range of rotational motion of the tanning unit, the instantaneous applied torque produced by said means for applying torque to said tanning unit approximately counter-balances the instantaneous torque produced by a gravitational force acting on said tanning unit.

It is yet another object of the present invention to provide an apparatus for supporting a tanning unit which is not sensitive to changes in ambient temperature.

Furthermore, it is an object of the present invention to provide an apparatus for unobtrusively supporting a tanning unit which does not interfere with access to the tanning unit and contributes to the aesthetic appeal of the tanning unit.

Therefore, in accordance with the objects of the present invention, an apparatus is provided for counter-balancing a tanning unit pivotally mounted to a base and having a radiation energy source for artificially tanning a person. The apparatus comprises: (a) a base; (b) a tanning unit pivotally mounted to the base along a pivot axis so that the tanning unit can be moved between a lowered position and a raised position; and (c) a means for variably applying torque to said tanning unit. Throughout the range of rotational motion of said tanning unit, the instantaneous applied torque produced by said means for applying torque to said tanning unit approximately counter-balances the instantaneous torque produced by a gravitational force acting on said tanning unit whereby said tanning unit may be retained in any instantaneous position between the lowered position and the raised position.

Further in accordance with the objects of the present invention, a tanning bed is provided having a counter-balanced top tanning unit pivotally mounted to a base and having a radiation energy source for artificially tanning a person. The tanning bed comprises: (a) a base; (b) a bottom tanning unit supported by a base; and (c) a rotating means pivotally mounted to the base along a pivot axis. The rotating means comprises a lifting means; a first lever means; a second lever means. A top tanning unit is attached to said rotating means so that said top tanning unit can be moved between a first raised position and a second lowered position. An optional brake means between said base and said rotating means provides friction resistance to rotational motion of the rotating means about the pivot axis. A first urging means is attached between said first lever means and said base so that, throughout the range of rotational motion of said first lever means, the line of action of said first urging means remains approximately perpendicular to the pivot axis and approximately perpendicular to the shortest line between the pivot axis and the line of action of the first urging means. A second urging means is attached between said second lever means and said base so that, throughout the range of rotational motion of said second lever means, the line of action of said second urging means changes from approximately intersecting the pivot axis to approximately perpendicular to the pivot axis and approximately perpendicular to the shortest line between the pivot axis and the line of action of the second urging means. The first and second urging means are designed so that, throughout the range of rotational motion of said rotating means, the sum of the instantaneous torques produced by said first urging means and said second urging means acting on said first lever means and said second lever means, respectively, approximately counter-balances the instantaneous torque produced by gravitational forces acting on the tanning unit attached to the lifting means. The optional brake means exerts frictional force to balance any differences between the opposing torques. Throughout the range of rotational motion of the rotating means, the top tanning unit is retained at any instantaneous position in static equilibrium.

Further objects and advantages of the present invention will become apparent to those skilled in the art upon studying the following detailed description of the present invention.

BRIEF DESCRIPTION OF THE DRAWING

The following figures of the drawing illustrate preferred embodiments of an apparatus of the present invention for counter-balancing a pivotally mounted lifting means where the axis of the pivot is perpendicular to gravitational forces:

FIG. 3a-c is three elevational views of a preferred embodiment of a tanning bed having the counter-balancing apparatus of the present invention (tanning units not shown) wherein the lifting means is in a lowered position.

DETAILED DESCRIPTION OF THE PRESENT INVENTION

Figure 1:
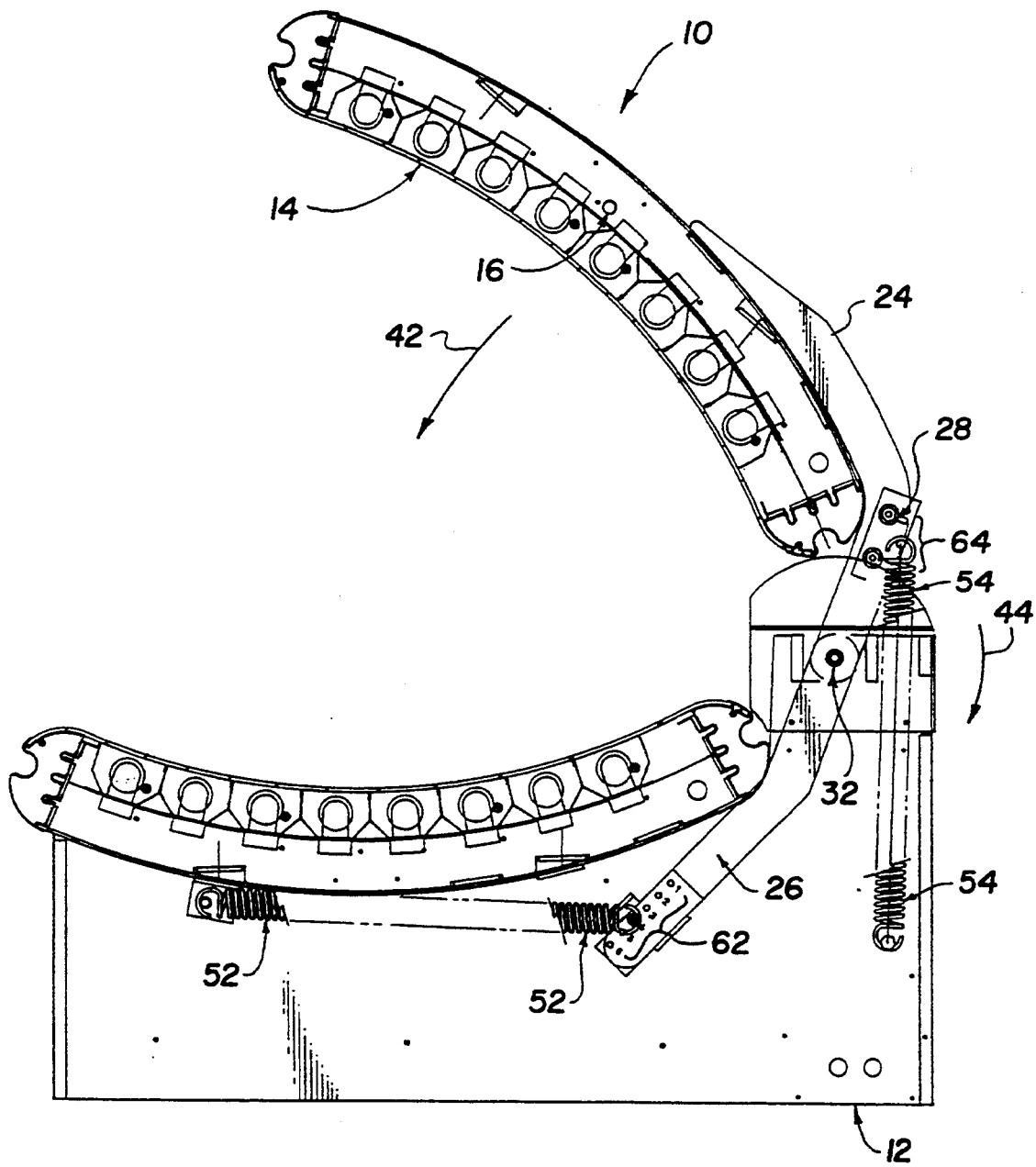
FIG. 1 is an elevational view in the plane perpendicular to the axis of rotation of a preferred embodiment of a tanning bed having the counter-balancing apparatus of the present invention wherein the top tanning unit is in a raised position.

The invention is described with reference to FIGS. 1-5 of the drawing wherein like numerals refer to like parts throughout the figures of the drawing.

Figure 2:
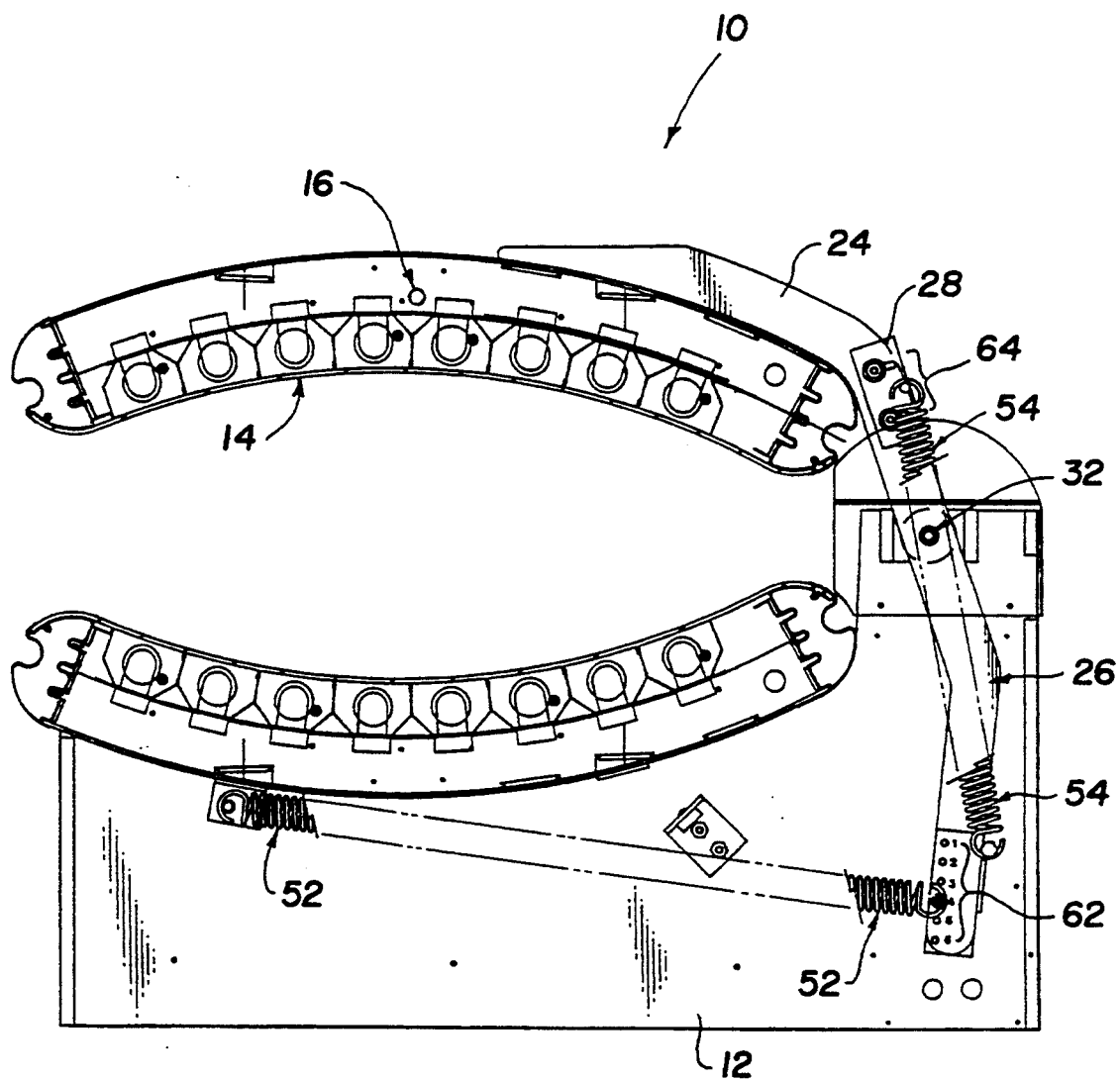
FIG. 2 is an elevational view in the plane perpendicular to the axis of rotation of a preferred embodiment of a tanning bed having the counter-balancing apparatus of the present invention wherein the top tanning unit is in a lowered position.

FIGS. 1 and 2 illustrate a tanning bed for artificially tanning a person incorporating a preferred embodiment of the apparatus of the present invention. The tanning bed, having a bottom and top tanning units, is generally referred to by the numeral 10. Top tanning unit 14 is pivotally mounted along a pivot axis 32 onto a base 12. In this particular embodiment, the tanning unit 14 is pivotally mounted to the base through lifting means 24. FIG. 1 illustrates the tanning unit 14 in a raised position and FIG. 2 illustrates the tanning unit 14 in a lowered position. The tanning unit 14 rotates such that the torque 42 caused by gravitational forces (not represented) acting on the tanning unit 14 increases as the angle of the moment arm (not represented) of the torque between the center of gravity 16 of the tanning unit and the pivot axis 32 increases relative to the gravitational forces.

For the purposes of the present description, the force exerted by a gravitational forces on the mass of the tanning unit 14 is assumed to operate through the center of gravity 16 of the tanning unit 14. All other forces are similarly assumed to operate at some instantaneous point throughout the range of rotational motion of the tanning unit 14. Similarly, all points of attachment are assumed to operate at a single point. The references to particular points are representative only and are not intended to limit the invention thereby. The present invention contemplates that forces and points of attachment may be accomplished at points, along axes, across surfaces, or through bodies. The present invention also contemplates that several points of attachment instead of a single point of attachment may be employed to advantage. For example, FIG. 3a-c of the drawing illustrates that the tanning unit 14 or the lifting means 24 can be attached at two or more points along the pivot axis 32.

Torque is the rotational tendency of a force acting about an axis. To determine the torque about an axis, at any point on the action line of the force, resolve the force into two rectangular components, one being parallel to the axis, the other being perpendicular to the axis. The torque is equal to the product of the perpendicular component and the perpendicular distance between the axis and the action line of the force. To facilitate calculations, the action line of the force can be resolved into three rectangular components, one being parallel to the axis, the other two components being perpendicular to the axis and to each other; then the total torque is equal to the sum of torques of the two components which are perpendicular to the axis. If one of the components of the action line of the force which is perpendicular to the pivot axis is chosen to intersect with the pivot axis, then the torque caused by the force is equal to the product of the other perpendicular component and the perpendicular distance to the axis. For the purposes of the present discussion, unless otherwise indicated, the component of the force which is perpendicular to the axis shall refer to the perpendicular component which is also perpendicular to the component of the force which intersects the pivot axis. For the purposes of the present discussion, the moment arm refers to the shortest line between the pivot axis and the perpendicular component of the force which is also perpendicular to the component of the force which intersects the pivot axis. For example, the line between the pivot axis 32 and the center of gravity 16 of the tanning unit 14 is the moment arm, regardless of the angle of any connecting structure such as the lifting means 24.

For the purposes of illustration, FIGS. 1-5 assume the axis of the pivot 32 is substantially perpendicular to the gravitational forces. However, the apparatus of the present invention works equally well where the axis of the pivot 32 relative to the gravitational forces 44 forms any angle less than 90 degrees. Of course, the torque produced by a gravitational forces acting on a tanning unit 14 is reduced as the axis of the pivot 32 relative to the gravitational forces approaches zero degrees because the component of the gravitational force which is perpendicular to the axis of the pivot 32 is reduced.

The tanning unit 14 may be attached directly to the pivot axis 32 or it may be connect to the pivot axis 32 through a lifting means 24. The lifting means 24 is part of a rotating member used to translate various urging forces into torque on the tanning unit 14. Hence, the rotating member comprises the lifting means 24 and at least one lever means 26.

The lifting means 24 is any structure for supporting the tanning unit 14 and connecting the tanning unit 14 to the base 12 along pivot axis 32. The moment arm of the torque 42 caused by gravitational forces acting on the tanning unit 14 is the line between the center of gravity 16 of the tanning unit 14 and the pivot axis. The actual structure of the lifting means 24 is irrelevant except for its ability to transfer a component of the gravitational force acting on the tanning unit 14 to the pivot axis 32 as torque 42. Therefore, the lifting means 24 is assumed to have negligible mass or the mass of the lifting means 24 is added to the mass of the tanning unit 14 for the purposes of determining the mass and center of gravity 16 of the tanning unit 14. The effective length or moment arm of the lifting means 24 is the perpendicular distance between the pivot axis 32 and the center of gravity 16 of the tanning unit 14.

The lever means is similarly defined. It includes any structure for transferring counter-balancing torque 44 to the tanning unit 14. Torque 44 is produced by the components of forces produced by at least one urging means, e.g., first urging means 52 and second urging means 54, which act through a lever means, e.g., first lever means 26 and second lever means 28, to the pivot axis 32. The actual structure of the lever means is irrelevant except for its ability to transfer a component of a balancing force acting on the lever means to the axis of the pivot 32 as torque 44. Therefore, the lever means is assumed to have negligible mass or the lever means is added to the tanning unit 14 for the purposes of determining the mass and center of gravity 16 of the tanning unit 14. The effective length or moment arm of the lever means is the shortest perpendicular distance between the pivot axis 32 and the line of action of an urging means, e.g., first urging means 52 and second urging means 54.

A counter-balancing torque 44 is transferred through the lever means to the tanning unit 14 about the pivot axis 32. The torque 44 approximately counter-balances the torque 42. Torque 44 is produced by at least one urging means attached between the lever means and the base 12 at a point remote from the axis of the pivot 32.

Throughout the range of rotational motion of the tanning unit 14, the urging means is in no case stressed beyond its elastic limit and it is subject to Hooke's law. The elastic limit is the limit of stress within which the deformation completely disappears after the removal of the stress. Hook's law states that, within the elastic limit, stress is proportional to deformation. Stress is force distributed internally within the material of the urging means; it is the internal mechanical reaction of the material accompanying deformation. Stresses always occur as pairs of opposing forces. Normal stresses are tensile stress and compressive stress, as opposed to tangential or shearing stress. The urging means for use in the present invention may take advantage of any type of stress, or any combination thereof. The urging means comprising a metallic spring illustrated in FIGS. 1, 2, and 3a-c of the drawing employ tensile stress.

Figure 4A:
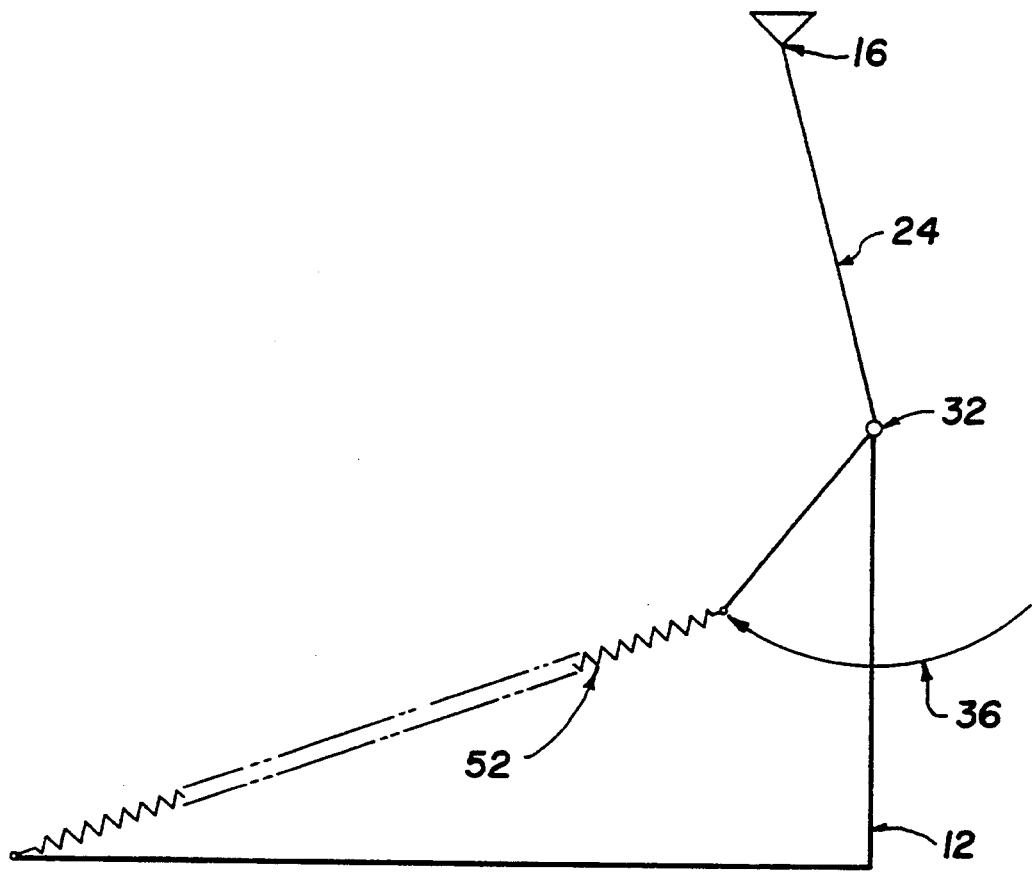
FIGS. 4a and 4b are simple diagrams in the plane perpendicular to the axis of rotation of the apparatus of the present invention having a single urging means and representing the motion of the lifting means.
Figure 4B:
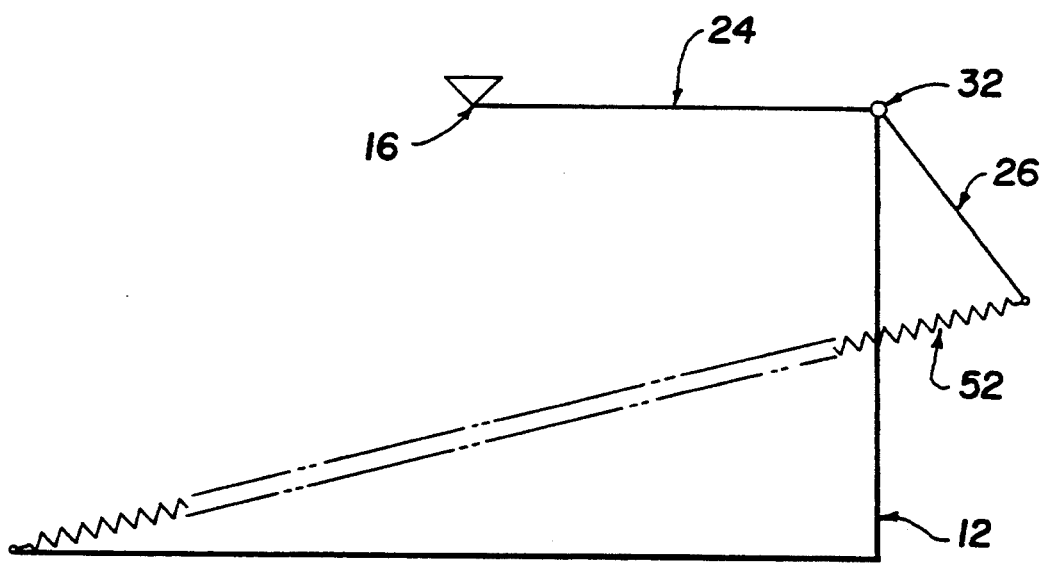
Figure 5A:
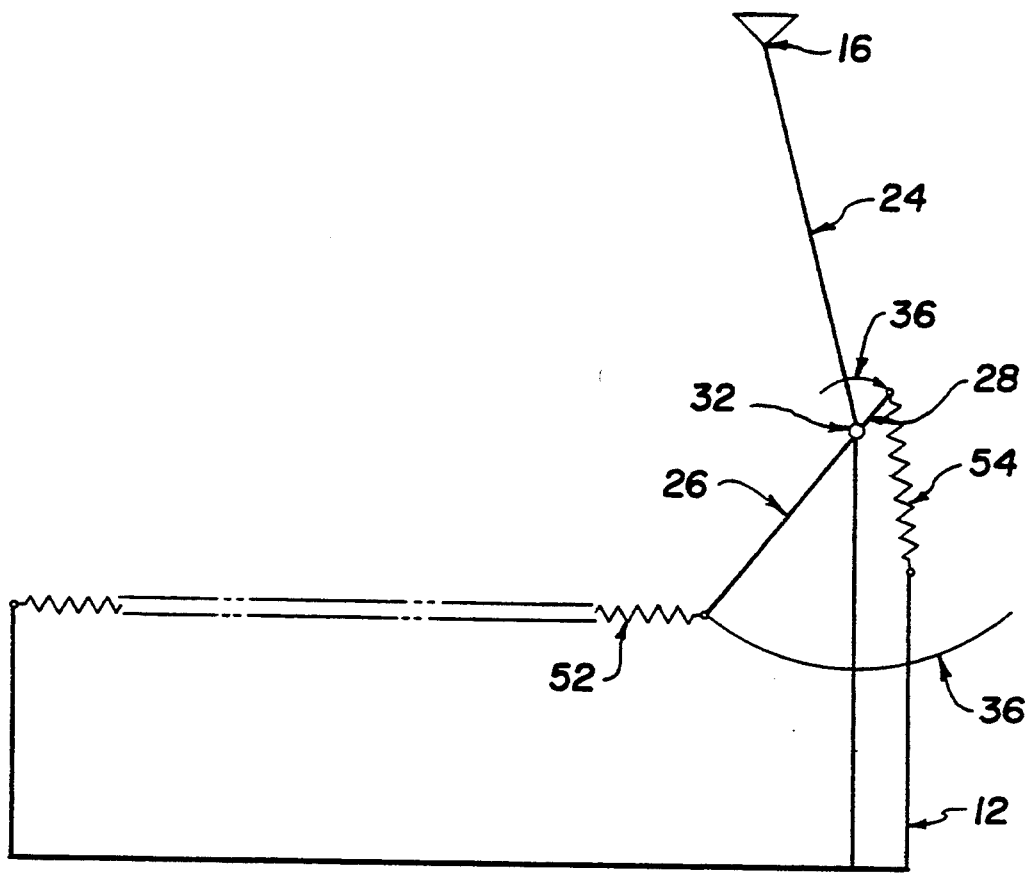
FIGS. 5a and 5b are simple diagrams in the plane perpendicular to the axis of rotation of the apparatus of the present invention having two urging means and representing the motion of the lifting means.
Figure 5B:
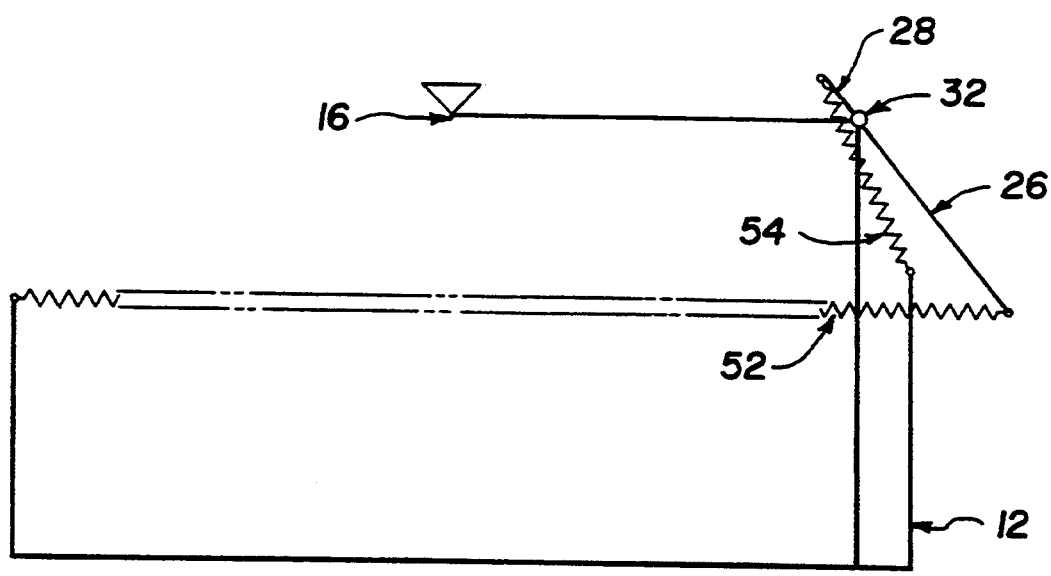

FIGS. 4a, 4b, 5a, and 5b represent simple diagrams of the present invention. FIGS. 4a and 4b illustrate one embodiment of the present invention employing a single urging means, for convenience referred to as a first urging means 52, connected to the tanning unit through a lever means, for convenience referred to as first lever means 26. FIGS. 5a and 5b illustrate a preferred embodiment of the present invention employing two urging means, referred to as a first urging means 52 and a second urging means 54, connected to the tanning unit through two lever means, referred to as a first lever means 26 and a second lever means 28. As best illustrated in FIGS. 4a and 5a of the drawing, the urging means is attached to the lever means so that when the tanning unit 14 rotates within its range of rotational motion, the point of attachment to the lever means moves through a particular arc 36 and causes the urging means, e.g., first urging means 52 (FIGS. 4a and 5a) and second urging means (FIG. 5a only), to mechanically deform. The range of deformation is kept within the elastic limit of the material of the urging means. As the material of the urging means deforms, the stress produced is translated through the lever means, e.g., lever means 26 (FIGS. 4a, 4b, 5a, and 5b) and lever means 28 (FIGS. 5a and 5b only), to the axis of rotation of the rotating member as torque 44.

Torque, as hereinbefore described, is a function of the perpendicular distance between the axis of rotation and the action line of the force, i.e., the effective length or moment arm of the lifting means 24 or the lever means, e.g., first lever means 26 and second lever means 28. In other words, if the magnitude of the force remains constant and orientation of the force relative to the pivot axis remains constant, the longer the moment arm, the larger the torque. Torque is also a function of the component of the force which is perpendicular to the axis of rotation. Therefore, if the orientation of the line of action of the force relative to the pivot axis changes, then the applied torque also changes. Of course, torque is a function of the magnitude of the component of an action line of a force which is perpendicular to the axis of rotation. In other words, the larger the component of an action line of a force which is perpendicular to the axis of rotation, the larger the torque. To the extent the angle between the action line of the force and the axis of rotation approaches 90 degrees, the larger the force, the larger the torque. All of these statements are simply different ways of expressing the nature of torque.

The nature of torque can be combined with the nature of a means forming an elastic spring which obeys Hook's law to provide an apparatus which varies the instantaneous torque applied to an axis of rotation. The instantaneous torque is the torque existing at any particular point throughout the range of the rotational motion of the rotating member.

The torque 42 varies as the tanning unit rotates about the pivot axis 32 because the perpendicular distance between (a) the component of the gravitational force acting on the tanning unit which is perpendicular to the pivot axis 32 and (b) the pivot axis 32 varies as the angle of the moment arm changes relative to the gravitational forces.

The counter-balancing torque 44 is varied by a different means. The objects of the present invention are accomplished by attaching the appropriate urging means, e.g., a metallic spring with appropriate elastic properties, to a lever means of a rotating member to create a torque 44 which approximately counter-balances the torque 42 created by the gravitational forces acting on the tanning unit 14.

Referring to FIGS. 4a and 4b of the drawing, the magnitude of the force produced by deforming the urging means 52 varies as the material of the first urging means 52 is deformed. Furthermore, the orientation of the action line of the force relative to the pivot axis 32 varies as the first lever means 26 rotates through its range of rotational motion. Therefore, torque 44 is increased for both reasons. These two factors can be designed so that they approximately counter-balance torque 42. This can be accomplished by attaching the first urging means 52 to the base 12 at a point such that when the first lever means 26 moves through its range of rotational motion, the force caused by the stress resulting from the deformation of the material of the first urging means 52 increases and so does the orientation of the action line of the force relative to the pivot axis 32.

In some circumstances, the torque 44 can be made to more closely approximate the torque 42 by employing more than one urging means. Referring now to FIGS. 5a and 5b of the drawing, the magnitude of the force produced by deforming the first urging means 52 varies as the material of the first urging means 52 is deformed. However, the orientation of the action line of the force relative to the pivot axis 32 remains substantially constant as the first lever means 26 rotates through its range of rotational motion. Therefore, torque 44 is increased substantially because of the change in magnitude of the force, not the minor change in orientation of the force relative to the pivot axis 32.

However, torque 44 produced by the first urging means may not vary as desired so as to approximate the torque 42. The first urging means 52 may produce a torque 44 which is too great toward one end of the range of rotational motion and to small toward the other end of the range. Therefore, a second urging means 54 is employed to apply a torque which when combined with the torque produced by the first urging means 52, produces a combined torque 44 which does approximate the instantaneous torque 42. The magnitude of the force produced by deforming the second urging means 54 remains substantially constant because the degree of deformation of the material of the second urging means 54 remains substantially constant. However, the orientation of the action line of the force relative to the pivot axis 32 is substantially varied as the second lever means 28 rotates through its range of rotational motion. The orientation of the line of action of the force produced by the second urging means 54 may range from intersecting the pivot axis 32 to being oriented perpendicular to the pivot axis 32 and perpendicular to a line intersecting the pivot axis 32. The torque produced by the second urging means 54 varies as a function of orientation. Therefore, the combined torque 44 can be designed to approximately counter-balance torque 42.

The arrangement and combination of elements in the apparatus of the present invention provides a means for approximately counter-balancing the instantaneous torque 42 against the instantaneous torque 44. It should be apparent to one skilled in the art that the urging means may be connected between the lever means and the base so that both the magnitude of the force caused by deforming the urging means and the line of action of the force change simultaneously and substantially, thereby achieving the objects of the present invention.

Sometimes it is difficult to perfectly counter-balance the tanning unit 14. Therefore, a brake means may be advantageously employed to apply friction resistance to rotational motion of the tanning unit 14 about the pivot axis 32. This brake means assures that the tanning unit 14 is maintained in static equilibrium at any desired position throughout its range of rotational motion. One example of a simple and efficient brake means for applying friction resistance is a simple washer system 20, best illustrated in FIG. 3a-c of the drawing. The washer 20, made of nylon or other suitable material, may be placed between the base 12 and the tanning unit 14. Friction resistance can be adjusted simply by tightening the attachment means, such as the nut and bolt illustrated in the drawing.

It is also very important to be able to manually adjust the variable torque 44. During typical manufacturing process, the exact mass and center of gravity of the tanning unit will vary. Furthermore, it would be advantageous to be able to use the same basic apparatus to support different models of tanning units having substantially different masses and centers of gravity. Therefore, as best illustrated in FIGS. 1, 2, and 3a-c of the drawing, a means for adjusting the point of attachment of the first urging means 52 and the second urging means 54 to the lever means 26 and 28, respectively, is provided. First adjustment means 62 comprises a series of pre-formed points of attachment for the first urging means 52 on the lever means 26 so that the line of action of the first urging means 52 may be adjusted. Second adjustment means 64 comprises a sliding point of attachment for the second urging means 54 on the second lever means 28 so that the line of action of the second urging means 54 may be adjusted.

If the orientation of the action line of the force produced by deforming the first urging means 52 or second urging means 54 is varied relative to the pivot axis 32 as the tanning unit 14 rotates throughout its range of rotational motion, it provides a manually adjustable variable for counter-balancing the instantaneous torque 42 created by the gravitational forces acting on the tanning unit 14 as it rotates about the pivot axis 32.

Finally, the means for applying torque can be designed so that it unobtrusively operates from the side of the tanning unit opposite to the access side of the tanning unit. Furthermore, the means for applying torque can be hidden in the supporting leg of the tanning unit, thereby increasing the aesthetic appeal of the tanning unit. See FIGS. 1-5.

It would also be valuable if the counter-balancing mechanism would tend to force the tanning unit 14 toward one end of its range of rotational motion and retain the tanning unit 14 at that end of its range of rotational motion. The apparatus of the present invention can accomplish this object of the present invention by adjusting the instantaneous counter-balancing torque 44 such that as the tanning unit 14 rotates toward the desired end of the range of rotational motion, the instantaneous torque 42 created by the gravitational forces acting on the tanning unit 14 becomes substantially not counter-balanced by torque 44. The tanning unit of this apparatus can be rotated in response to the least force in that portion of its range of rotational motion which is substantially counter-balanced by torque 44, whereas more force is required to rotate the tanning unit 14 away from its least counter-balanced position.

Similarly, it would be valuable if the counterbalancing mechanism would tend to force the tanning unit 14 toward either end of its range of rotational motion and retain the tanning unit 14 at either end of its range of rotational motion. The apparatus of the present invention accomplishes this object of the present invention by adjusting the instantaneous counter-balancing torque 44 such that the instantaneous torque 42 created by the gravitational forces acting on the tanning unit 14 is approximately counter-balanced by torque 44 only somewhere between the two ends of its range of rotational motion. The instantaneous counter-balancing torque 44 is adjusted so that as the tanning unit 14 rotates toward either end of its range of rotational motion, the instantaneous torque 44 created by the gravitational forces acting on the tanning unit 14 becomes substantially not counter-balanced by torque 44. Therefore, the tanning unit 14 of this apparatus can be rotated in response to the least force at the most counter-balanced point, whereas more force is required to rotate the tanning unit 14 at either end of its range of rotational motion.

What is claimed is:
1. A tanning bed having a counter-balanced top tanning unit pivotally mounted to a base and having a radiation energy source for artificially tanning a person where the tanning bed comprises:

(a) a base;

(b) a bottom tanning unit supported by said base;

(c) a rotating means pivotally mounted to the base along a pivot axis, the rotating means comprising (i) a lifting means; (ii) a first lever means; and (iii) a second lever means;

(d) a top tanning unit attached to said lifting means so that said top tanning unit can be moved between a first raised position and a second lowered position;

(e) a first urging means attached between said first lever means and said base so that, throughout the range of rotational motion of said first lever means, the line of action of said first urging means remains approximately perpendicular to the pivot axis and approximately perpendicular to the shortest line between the pivot axis and the line of action of the first urging means; and (f) a second urging means attached between said second lever means and said base so that, throughout the range of rotational motion of said second lever means, the line of action of said second urging means changes from approximately intersecting the pivot axis to approximately perpendicular to the pivot axis and approximately perpendicular to the shortest line between the pivot axis and the line of action of the second urging means;

wherein, throughout the range of rotational motion of said rotating means, the sum of the instantaneous torques produced by said first urging means and said second urging means acting on said first lever means and said second lever means, respectively, approximately counter-balances the instantaneous torque produced by gravitational forces acting on the top so that the top tanning unit is retained at any instantaneous position in static equilibrium.

2. The apparatus of claim 1 further comprising a brake means between said base and said rotating means which provides friction resistance to rotational motion of the rotating means about the pivot axis.

3. An apparatus for counter-balancing a tanning unit pivotally mounted to a base and having a radiation energy source for artificially tanning a person where the apparatus comprises:

(a) a base;

(b) a tanning unit pivotally mounted to the base along a pivot axis so that the tanning unit can be moved between a lowered position and a raised position;

(c) a first urging means and a second urging means, the first and second urging means being connected between said tanning unit and said base so that, throughout the range of rotational motion of the tanning unit, said first urging means applies a first force vector to the tanning unit as a function of the rotational position of said tanning unit and so that a substantial component of the first force vector remains oriented substantially perpendicular to the pivot axis and substantially perpendicular to the shortest line between the pivot axis and the first force vector, and said second urging means applies a second force vector having a substantially constant magnitude to the tanning unit so that a substantial component of the second force vector changes orientation between (i) substantially perpendicular to the pivot axis and substantially perpendicular to the shortest line between the pivot axis and the force vector and (ii) substantially parallel to the pivot axis or substantially parallel to the shortest line between the pivot axis and the second force vector, whereby said first and second urging means apply an instantaneous torque to said tanning unit that approximately counter-balances the instantaneous torque produced by a gravitational force acting on said tanning unit.

4. The apparatus of claim 3 wherein (a) said first urging means applies an increasing torque to said tanning unit as said tanning unit moves from the lowered position to the raised position; and (b) said second urging means apples a decreasing torque to said tanning unit as said tanning unit moves from the lowered position to the raised position.

5. The apparatus of claim 3 additionally comprising a means for adjusting the amount of variable torque applied by said first urging means.

6. The apparatus of claim 3 additionally comprising a means for adjusting the amount of variable torque applied by said second urging means.

7. An apparatus for counter-balancing a tanning unit pivotally mounted to a base and having a radiation energy source for artificially tanning a person where the apparatus comprises:

(a) a base;

(b) a tanning unit pivotally mounted to the base along a pivot axis so that the tanning unit can be moved between a lowered position and a raised position;

(c) a first urging means and a second urging means, the first and second urging means being connected between said tanning unit and said base so that, throughout the range of rotational motion of the tanning unit, said first urging means applies a force vector having a substantially variable magnitude to the tanning unit so that a substantial component of the force vector remains oriented substantially perpendicular to the pivot axis and substantially perpendicular to the shortest line between the pivot axis and the variable magnitude force vector, and said second urging means applies a force vector having a substantially constant magnitude to the tanning unit so that a substantial component of the force vector changes orientation between (i) substantially perpendicular to the pivot axis and substantially perpendicular to the shortest line between the pivot axis and the force vector and (ii) substantially parallel to the pivot axis or substantially parallel to the shortest line between the pivot axis and the force vector whereby the instantaneous applied torque produced by said first and second urging means on said tanning unit approximately counter-balances the instantaneous torque produced by a gravitational force acting on said tanning unit; and (d) a means for applying sufficient friction resistance to the rotational motion of said tanning unit to substantially over-balance any differences between the instantaneous applied torque produced by said first urging means and said second urging means to said tanning unit and the instantaneous torque produced by a gravitational force acting on said tanning unit whereby said tanning unit may be retained in any instantaneous position between the lowered position and the raised position.

8. The apparatus of claim 7 wherein
(a) said first urging means applies an increasing torque to said tanning unit as said tanning unit moves from the lowered position to the raised position; and
(b) said second urging means applies a decreasing torque to said tanning unit as said tanning unit moves from the lowered position to the raised position.

9. The apparatus of claim 7 additionally comprising a means for adjusting the amount of variable torque applied by said first urging means.

10. The apparatus of claim 7 additionally comprising a means for adjusting the amount of variable torque applied by said second urging means.

* * * * *